| United States Patent [19] | [11] Patent Number: 4,885,244 |
| Miyamori et al. | [45] Date of Patent: Dec. 5, 1989 |

[54] METHOD OF PRODUCING HYALURONIC ACID

[75] Inventors: Takao Miyamori; Ryozo Numazawa; Akihiro Sakimae; Hisao Onishi, Tokyo, all of Japan

[73] Assignee: Mitsubishi Rayon Co., Ltd., Tokyo, Japan

[21] Appl. No.: 104,219

[22] Filed: Oct. 5, 1987

[30] Foreign Application Priority Data

Oct. 9, 1986 [JP] Japan ................................. 61-240904
Dec. 16, 1986 [JP] Japan ................................. 61-299191
May 6, 1987 [JP] Japan ................................. 62-110157

[51] Int. Cl.$^4$ .......................... C12P 19/04; C07H 5/04
[52] U.S. Cl. .................................. 435/101; 536/55.1; 436/123
[58] Field of Search ...................... 435/101; 436/123; 536/55.1

[56] References Cited

U.S. PATENT DOCUMENTS 4,517,295  5/1985  Bracke et al. ....................... 435/801
4,780,414 10/1988  Nimrod et al. ...................... 435/803

Primary Examiner—Ronald W. Griffin
Assistant Examiner—Pamela S. Webber
Attorney, Agent, or Firm—Oblon, Spivak, McClelland, Maier & Neustadt

[57] ABSTRACT

High molecular weight hyaluronic acid can be efficiently produced by incorporating one or more compounds having at least one aromatic ring to which one or more hydroxyl groups are attached into a medium for producing hyaluronic acid by a bacterium capable of producing hyaluronic acid. By using this method, a sufficient amount of hyaluronic acid can be easily obtained without decomposing the high molecular structure of hyaluronic acid so that the process for isolating and purifying hyaluronic acid from the medium can be simplified.

3 Claims, No Drawings

METHOD OF PRODUCING HYALURONIC ACID

BACKGROUND OF THE INVENTION

1. Field of the Invention

This invention relates to a process for producing hyaluronic acid by using microorganisms.

Hyaluronic acid, one of such expensive glycosaminoglycans as chondroitin sulfate and heparin, is widely distributed in connective tissues of mammalians in only small quantities and is also known to present in microorganisms.

Highly pure hyaluronic acid preparations extracted from the aforementioned sources are highly viscous, effectively retain the moisture and have wound healing properties, so that they have been extensively in use as cosmetic constituents, supportive media in ophthalmic surgery and remedies for joint inflammation.

2. Description of the Prior Art

Conventionally, hyaluronic acid has been obtained industrially by extraction from rooster combs, bovine joints or whale cartilages. In addition, a process of obtaining hyaluronic acid from microorganisms has been disclosed in the Japanese Patent Laid-Open No. 58-56692 in which bacteria capable of producing hyaluronic acid are cultured and hyaluronic acid is purified from the culture.

However, the above-mentioned method of extracting hyaluronic acid from the animal tissues has various disadvantages and it is difficult to obtain hyaluronic acid effectively and in abundance by using this method.

For example, hyaluronic acid is present in the tissues in only tiniest traces and furthermore, it forms a complex with proteins or other mucopolysaccharides, therefore, complicated and delicate purification processes including procedures for removing proteins and for isolating other mucopolysaccharides are indispensable to obtain pure hyaluronic acid. In addition, hyaluronidase is often found in the extracting process of this method, which results in degradation of hyaluronic acid during the extracting process to give hyaluronic acid having a low molecular weight which brings disadvantageous properties such as poor moisture retaining capacity and low viscosity.

On the other hand, the method of purifying hyaluronic acid from the culture of bacteria capable of producing hyaluronic acid has an advantage that the purification process tends to be simple as compared to the aforementioned method for extraction from the animal tissues, since a protein-free medium is used for culturing bacteria capable of producing hyaluronic acid in the culture method to obtain hyaluronic acid.

However, even this method has a disadvantage that only low molecular weight hyaluronic acid can be obtained and the amount of hyaluronic acid produced per culture volume is low, since hyaluronidase is excreted by bacteria capable of producing hyaluronic acid during the culture.

SUMMARY OF THE INVENTION

In order to provide solution for the problems in the method of using bacteria capable of producing hyaluronic acid, in which hyaluronic acid of a high molecular weight can be obtained, the present inventors have been made several efforts. As a result, the present invention has been accomplished on the basis of the discovery that high molecular weight hyaluronic acid can be efficiently produced by causing bacteria capable of producing hyaluronic acid to produce hyaluronic acid in the presence of one or more compounds having at least one aromatic ring to which one or more hydroxyl groups are attached.

The object of the present invention is to provide a method of efficiently producing hyaluronic acid having a high molecular weight.

Another object of the present invention is to provide a method of producing hyaluronic acid in which an increased amount of hyaluronic acid per culture volume is obtainable.

A further object of the present invention is to provide a method of producing hyaluronic acid at small cost by simplifying processes of isolation and purification, in which proteins form complexes with the compound having at least one aromatic ring to which one or more hydroxyl groups are attached and the resulting complexes can be more easily removed.

These objects of the invention have been accomplished by means of adding one or more compounds having at least one aromatic ring to which one or more hydroxyl groups are attached to the media for producing hyaluronic acid by bacteria capable of producing hyaluronic acid.

According to the method of the present invention for producing hyaluronic acid, hyaluronic acid of a high molecular weight is obtainable, in which the activity of hyaluronidase produced in the medium is suppressed by the effect of the small amount of the compounds with hydroxyl groups attached to aromatic rings so as to accumulate high molecular weight hyaluronic acid in the medium. Further, the hyaluronic acid according to the present invention is found to be appropriate for the use in cosmetics or medicines.

In accordance with the present invention, when hyaluronic acid is produced by culturing bacteria capable of producing hyaluronic acid, the hyaluronic acid productivity and quality thereof can be improved simply by adding a small amount of the compounds with hydroxyl groups attached to aromatic rings in an ordinary culturing process. In addition, in a method where saccharide is converted into hyaluronic acid by bringing cultured bacteria into contact with saccharide, highly-pure hyaluronic acid is obtained by isolating and purifying hyaluronic acid by using simple procedures as compared to those in the method of excreting hyaluronic acid in the culture medium.

DETAILED DESCRIPTION OF THE INVENTION

A method of producing hyaluronic acid according to the present invention includes a process to accumulate hyaluronic acid, in which bacteria capable of producing hyaluronic acid are brought into contact with saccharide in an aqueous medium containing one or more compounds having at least an aromatic ring to which one or more hydroxyl groups are attached.

Microorganisms capable of producing hyaluronic acid to be used in practicing the present invention are, for example, *Streptococcus pyogenes, S. equi, S. equisimilis, S. dysgalactiae, S. zooepidemicus* and *Pasteurella multocida.*

The compounds having at least one aromatic ring to which one or more hydroxyl groups are attached as used in the present invention denote the ones which have at least one phenolic backbone structure in the molecules and do not markedly interfere hyaluronic acid productivity and, preferably, microbial growth.

These compounds include, for example, monohydric phenols, e.g. phenol, cresol or xylenol; dihydric phenols, e.g. catechol, 4-methyl-pyrocatechol, urushiol, cresolcinol or orcinol; polyhydric phenols, e.g. pyrogallol, 1,2,4-benzenetriol, benzenetetraol or benzenehexaol; aromatic hydroxycarboxylic acids, e.g. gentisinic acid, 2,3-dihydroxybenzoic acid, gallic acid, salicylic acid, protocatechuic acid, pyrogallol-4-carboxylic acid or 3-o-galloylgallic acid, and esters thereof; aromatic aldehydes, e.g. vanillin, o-vanillin or protocatechualdehyde; heterocyclic compounds, e.g. catechin, luteolin, myricetin or anthocyanidin; non-condensed polycyclic compounds having phenolic hydroxyl groups, e.g. biphenyldiol or ellagic acid; naphthalene compounds having phenolic hydroxyl groups, e.g. naphthol or naphthalenediol; anthracene compounds having phenolic hydroxyl groups, e.g. chrysarobin or anthragallol; sulfosalicylic acid; vitamin P; 3,4-dihydroxyphenylalanine; and tannins. These compounds are used either singularly or as a mixture of the two or more. Furthermore, these compounds immobilized in water-insoluble carriers may also be used without difficulty. Among these compounds, tannins are preferably used and any tannins, such as hydrolysable tannins obtained from gall (gallic acid) or gallnut and condensed type tannins obtained from betel-nut palm or cinnamons, are used either singularly or as a mixture thereof. In general, tannins used in dyes, pigments or medicaments are practically applicable. Raw materials containing tannins or plant extracts without processing can also be used.

The concentrations of the above compounds in the medium are preferably more than 0.0001% by weight and can be increased so far as hyaluronic acid productivity is not reduced, as low concentrations tend to interfere the hyaluronic acid production in the medium and reduce the molecular weight of hyaluronic acid. When tannins are used as the above compound, the concentrations between 0.0001% and 0.5% by weight are preferable.

Further, saccharide, the major source of hyaluronic acid, to be used in the present invention are, for example, one of those selected from glucose, fructose, saccharose, lactose, galactose and a combination of UDP-N-acetylglucosamine and UDP-glucuronic acid, and N-acetylglucosamine. They can be used either singularly or as a mixture thereof.

In order to allow microorganisms to contact with saccharide in practicing the present invention, the microorganisms may be cultured in a medium containing saccharide or, alternatively, the microorganisms having been cultured may be brought into contact with saccharide under non-culturing conditions.

The non-culturing conditions as used herein are the conditions in which one or more nutrient sources other than sugars are not present in a medium in the amount sufficient for microbial growth.

In the culturing method, the medium comprises nitrogen sources and inorganic salts besides the above-mentioned compounds having hydroxyl groups attached to aromatic rings and saccharide, and furthermore organic trace elements and carbon sources other than saccharide, if necessary.

The nitrogen sources to be used are, for example, peptone, ammonium citrate, ammonium sulfate, any other amino acid mixtures and yeast extract. The inorganic salts to be added in the appropriate amounts are, for example, sodium chloride and phosphoric, sulfuric or carbonic salts of magnesium, potassium, iron or calcium. In addition, the vitamins in very small quantities are added, if necessary.

The carbon sources to be applicable other than saccharide are organic acids, such as fumaric acid.

In producing hyaluronic acid by using specified culture conditions, constituents for the medium are first dissolved in water and then sterilized to prepare the medium. Sterilization may be carried out by heating, filtration or irradiation. Unstable components may be sterilized separately to avoid degradation of the components. For example, saccharide and the compounds having hydroxyl groups attached to aromatic rings are sterilized separately from other medium components and are mixed together after the sterilization.

Bacteria capable of producing hyaluronic acid are then inoculated into this medium and incubation is carried out for 1-4 days under aerobic or anaerobic conditions at a temperature between 25° and 40° C. and at a pH between 5.5 and 8.5 to accumulate hyaluronic acid.

During the incubation, the compounds having hydroxyl groups attached to aromatic rings and/or carbon sources may be added in appropriate amounts. After the incubation, the bacteria are removed by centrifugation or filtration and, if necessary, low molecular weight substances are further removed by ultrafiltration or dialysis of the cell-free culture medium. Subsequently, the cell free culture medium thus obtained is subjected to a known step such as fractional precipitation by alcohol or graduation precipitation by surface-active agents to obtain purified hyaluronic acid.

In producing hyaluronic acid under the nonculturing conditions, the microorganisms capable of producing hyaluronic acid can be cultured in an ordinary medium for 1-4 days under aerobic or anaerobic conditions at a temperature between 25° and 40° C. and at a pH between 5.5 and 8.5 and the bacterial cells can be then obtained by filtration or by centrifugation.

The microbial cells thus separated from the culture are resting cells of the microorganisms obtained by a solid-liquid separating method, such as centrifugation and filtration. If necessary, the cells of the microorganisms are washed with water, buffer solutions or saline after the separation from the culture.

The method, in which bacterial cells are brought into contact with saccharide in a medium for reaction, comprises dissolving saccharide and one or more compounds having at least one aromatic ring to which one or more hydroxyl groups are attached in the medium for the contact, then suspending the microbial cells therein, and mixing the medium at the controlled temperature and pH.

The concentration of the cells in the medium is between 0.01% and 5% by dry weight, the concentration of saccharide is between 0.1% to 20% by weight, and the temperature and pH are between 20° to 45° C., and between 5.5 to 8.0, respectively.

In converting saccharide to hyaluronic acid by bringing the bacterial cells into contact with saccharide as mentioned above, the activity of the hyaluronidase excreted into the reaction medium is suppressed by the compounds having hydroxyl groups attached to aromatic rings. As a result, high molecular weight hyaluronic acid can be efficiently accumulated in the medium.

The present invention will be more specifically described in the following examples and comparative examples.

In the following examples, S. equi or S. zooepidemicus is practically used as the bacterium capable of producing hyaluronic acid. However, the kind of the bacteria to be used as the bacteria capable of producing hyaluronic acid will not be limited to those described in the Examples hereinafter, since the important aspect of the present invention is the inhibiting action of the compounds having hydroxyl groups attached to aromatic rings against hyaluronidase and not the action to the hyaluronic-acid-producing bacteria themselves, consequently any effect of the present invention can be achieved independently of the kind of bacteria capable of producing hyaluronic acid to be used.

EXAMPLE 1

In 1.76 l of deionized water were dissolved 30 of peptone, 20 g of monopotassium phosphate, 10 g of sodium acetate (3H2O), 6 g of sodium hydrogen carbonate, 0.4 g of $MgSO_4 \cdot 7H_2O$, 0.02 of $FeSO_4 \cdot 7H_2O$, 0.02 g of $MnCl_2 \cdot 4H_2O$, 0.1 g of $CaCl_2$, and 10 g of yeast extract. After adjusting the pH to 7.0, the solution was sterilized by autoclaving at 121° C. for 20 minutes. To the solution were added aseptically 20 ml of a 1% by weight aqueous solution of tannic acid having been sterilized by membrane filtration (Millex-GS, Millipore) and 200 ml of a 30% by weight aqueous solution of glucose having been sterilized by autoclaving at 121° C. for 20 minutes.

Into the medium thus prepared was inoculated 20 ml of a preculture of S. equi (ATCC 9527) and the medium was then anaerobically incubated at 37° C. for 10 hours with rotation at 100 rpm. The pH of the medium was maintained at 7.0 by continuous addition of a NaOH aqueous solution (5.0M). After the incubation, 20 ml of 1% by weight aqueous tannic acid and 200 ml of 30% by weight aqueous glucose were further added and the medium was incubated for additional 14 hours. To the cultured medium was added 6 l of deionized water and the bacterial cells were then removed by centrifugation. The resulting cell-free medium was subjected to fractional precipitation by addition of 1.5 volumes of ethanol and the precipitate thus prepared was dissolved in a 0.1 M NaCl aqueous solution. The solution was filtered with addition of cetyl-pyridinium chloride and an unfiltrable portion was washed with 0.1 M NaCl and further with ethanol and then redissolved in 0.5 M NaCl containing 15% ethanol. To the solution was added 1.5 volumes of ethanol for fractional precipitation and the resultant precipitate was vacuum-dried at 50° C. for 5 hours. Hyaluronic acid powder of 11.0 g was thus prepared. The molecular weight of the hyaluronic acid was 2,500,000 daltons and the protein content was less than 0.03%.

COMPARATIVE EXAMPLE 1

The strain of S. equi (ATCC 9527) was cultured in the same medium and under the same conditions as described in Example 1, except that tannic acid was not added in the medium. After incubation for 10 hours, 200 ml of a 30% by weight aqueous solution of glucose was freshly added to the medium and the incubation was further continued for 14 hours. By a similar purification procedure as described in Example 1, 4.2 grams of purified hyaluronic acid powder was obtained.

The molecular weight of the hyaluronic acid thus obtained was 430,000 daltons and the protein content was 0.13%.

EXAMPLE 2

An aqueous solution, 1.76 l, containing 30 of peptone, 10 g of yeast extract, 20 g of monopotassium phosphate, 10 g of sodium acetate (3H2O), 6 g of sodium hydrogencarbonate, 0.4 g of magnesium sulfate (7H2O), 0.02 g of ferrous sulfate (7H2O), 0.02 g manganese sulfate (4H2O) and 0.1 g of calcium chloride (2H2O) and having the pH thereof adjusted to 7.0 was sterilized in a 3 l-volume jar-fermentor. To the medium thus prepared were added 200 ml of a 30% (w/v) glucose solution and 20 ml of a 1% (w/v) pyrogallol solution, each having been sterilized. After inoculation of 20 ml of a preculture of S. equi (ATCC 9527), the medium was incubated for 10 hours anaerobically with rotation at 100 rpm at 37° C. with the pH maintained at 7 by continuous addition of a NaOH aqueous solution (5.0M). Then, 120 ml of a 50% (w/v) glucose solution and 20 ml of a 1% (w/v) pyrogallol solution, both sterilized, was added and the incubation was further continued for 14 hours. To the resultant culture was added 6 l of deionized water and the culture was centrifuged to remove the cells. Then, to the cell-free culture, ethanol was added in the proportion of one volume of the cell-free culture to 1.5 volumes of ethanol to obtain precipitate. The resulting precipitate was dissolved in a 0.1M NaCl solution. The solution was filtered with addition of cetyl-pyridinium chloride and the resulting unfiltrable portion was washed with a 0.1M NaCl solution and further with ethanol and then redissolved in a 0.5M NaCl aqueous solution containing 15% ethanol. To the solution was added 1.5 volumes of ethanol for fractional precipitation and the resultant precipitate was vacuum-dried at 50° C. for 5 hours. Hyaluronic acid powder of 11.0 grams was thus prepared. The molecular weight of this hyaluronic acid was 2,000,000 daltons and the protein content was less than 0.03%.

EXAMPLES 3 TO 8

Hyaluronic acid was prepared in a similar manner as described in Example 2, except that other compounds shown in Table 1 were alternatively used for pyrogallol.

The yield and molecular weight of sodium hyaluronate obtained in Examples 3 to 8 were given in Table 1.

TABLE 1

| Example | Compound | Hyaluronic acid yield (g) | Mol. Wt. (X10$^4$) |
|---|---|---|---|
| 3 | Catechin | 10.5 | 200 |
| 4 | Vanillin | 10.5 | 180 |
| 5 | o-vanillin | 11.0 | 200 |
| 6 | Catechol | 11.0 | 200 |
| 7 | Phenol | 10.0 | 160 |
| 8 | Gentisinic acid | 10.3 | 180 |

EXAMPLE 9

An aqueous solution, 1.78 l, containing 30 g of peptone, 10 g of yeast extract, 20 g of monopotassium phosphate, 10 g of sodium acetate (3H2O), 6 g of sodium hydrogencarbonate, 0.4 g of magnesium sulfate (7H2O), 0.02 g of ferrous sulfate (7H2O), 0.02 g manganese sulfate (4H2O) and 0.1 g of calcium chloride (2H2O) and having the pH thereof adjusted to 7.0 was sterilized in a 3 l volume jar-fermentor. To the medium thus prepared were added 200 ml of a 30% (w/v) sterile aqueous solution of glucose and 20 ml of an inoculum of *S. equi* (ATCC 9527). The medium was anaerobically incubated at 37° C. at pH 7.0 for 10 hours and the resultant culture was then centrifuged to obtain bacterial cells.

The cells thus obtained (7 g by wet weight) were mixed with 10 g of glucose, 1.87 g of sodium glutamate, 0.2 g of magnesium chloride, 0.02 g tannic acid and 40 ml of a 1 M potassium phosphate buffer solution (pH 7.0) in a flask to give a total volume of 200 ml with deionized water. The mixture was then shaken for contact reaction for 4.5 hours at 37° C. with the pH maintained at 7.0. Subsequently, the mixture was diluted 10 times with deionized water and centrifuged to obtain a supernatant.

The supernatant was subjected to fractional precipitation by addition of 1.5 volumes of ethanol to obtain potassium hyaluronate precipitate. The precipitate thus prepared was dissolved in a 0.1M NaCl aqueous solution. The solution was filtered with addition of cetylpyridinium chloride and an unfiltrable portion was washed with 0.1 M NaCl aqueous solution and further with ethanol and then redissolved in 0.5 M NaCl aqueous solution containing 15% ethanol. To the solution was added 1.5 volumes of ethanol for fractional precipitation and the resultant precipitate was vacuum-dried at 50° C. Purified sodium hyaluronate of 0.6 g was thus prepared. The molecular weight of the hyaluronic acid based on viscosity measurements was 2,000,000 daltons and the protein content was 0.01% by weight.

COMPARATIVE EXAMPLE 2

The strain of *S. equi* was cultured in the same manner and under the same conditions as described in Example 9 and then the bacterial cells were obtained by centrifugation.

The cells thus obtained (7 g by wet weight) were mixed with 10 g of glucose, 1.87 g of sodium glutamate, 0.2 g of magnesium chloride and 40 ml of a 1M potassium phosphate buffer solution (pH 7.0) in a flask to give a total volume of 200 ml with deionized water. The mixture was then shaken for contact reaction for 4.5 hours at 37° C. with the pH maintained at 7. Subsequently, the mixture was diluted 10 times with deionized water and centrifuged to obtain a supernatant. The supernatant was treated in the same manner as described in Example 9 and 0.5 g of white-powdered sodium hyaluronate was obtained. The molecular weight of the sodium hyaluronate thus obtained was estimated to be 400,000 daltons by viscometric measurement.

EXAMPLE 10

In 1 l of deionized water were dissolved 30 g of peptone, 10 g of yeast extract, 20 g of monopotassium phosphate, 10 g of sodium acetate ($3H_2O$), 6 g of sodium hydrogencarbonate, 0.4 g of magnesium sulfate ($7H_2O$), 0.02 g of ferrous sulfate ($7H_2O$), 0.02 g manganese sulfate ($4H_2O$) and 0.1 g of calcium chloride ($2H_2O$) and the pH of the solution was adjusted to 7.0. The medium having the aforementioned constituents (1.8 l) was taken into a 3 l-volume jar-fermentor and sterilized by autoclaving at 121° C. for 20 minutes.

To the medium thus prepared in the jar-fermentor were added 120 ml of a 50% (w/v) glucose solution and 20 ml of a 1% (w/v) tannic acid solution, each having been sterilized under the conditions described above, and were further added 60 ml of a precultured inoculum of *S. equi* (ATCC 9527). The medium was then incubated at 37° C. with rotation at 100 rpm and aeration at 0.005 vvm (volume of air per volume of medium per minute). The pH of the culture was maintained at 7.0 by continuous addition of a NaOH solution (5.0M).

After incubation for 7 hours, 120 ml of a 50% (w/v) sterile glucose solution was added and further incubation was continued for 17 hours with continuous addition of a 0.2% (w/v) sterile tannic acid solution to the medium at a flow rate of 11.5 ml/hr.

After the incubation, the culture was treated for purification in the same manner as described in Example 1, and 11.0 g of purified sodium hyaluronate was finally obtained. The molecular weight of the hyaluronic acid thus prepared was 2,600,000 daltons.

EXAMPLE 11

The medium containing the same constituents as described in Example 10 was prepared and sterilized in a jar-fermentor as in Example 10. After inoculation with an inoculum of *S. equi* (ATCC 9527), the medium was cultured at 37° C. with rotation at 100 rpm and aeration at 0.005 vvm. The pH of the culture was maintained at 7.0 by continuous addition of a NaOH solution (5.0M).

After incubation for 7 hours, 120 ml of a 50% (w/v) sterile glucose solution was freshly added. Incubation was further continued for 17 hours with continuous addition of a 0.2% (w/v) sterile tannic acid solution in volume equivalent to the NaOH solution added for the pH control.

After the incubation, the culture was treated in the same manner as described in Example 1 to extract and purify sodium hyaluronate. Sodium hyaluronate thus obtained was 10.8 grams and the molecular weight thereof was 2,600,000 daltons.

EXAMPLE 12

Hyaluronic-acid-producing bacterium was cultured in the same manner as described in Example 10, except that the strain of the hyaluronic-acid-producing bacteria used was *S. zooepidemicus* (NCTC 7023). Sodium hyaluronate purified from the resulting culture in the same manner as described in Example 1 was 7.0 grams and has a molecular weight of 2,200,000 daltons.

COMPARATIVE EXAMPLE 3

Hyaluronic-acid-producing bacterium was cultured in the same manner as described in Example 12, except that tannic acid was not added. Sodium hyaluronate purified from the resultant culture in the same manner as described in Example 1 was 4.0 grams with a molecular weight of 600,000 daltons.

EXAMPLE 13

An efficient production of high molecular weight sodium hyaluronate can be expected by using *S. pyogenes* (ATCC 10389) as a hyaluronic-acid-producing bacterium in the same manner as described in Example 10, since the primary object of the present invention is to use inhibitory action of the compound having at least one aromatic ring to which one or more hydroxyl groups are attached upon hyaluronidase.

The strains mentioned in the above examples are deposited at the following agencies under the deposit number given in the parentheses after the species name and publicly available. The strains having an ATCC number are maintained in the American Type Culture Collection, 12301 Parklawn Drive, Rockville, Md. 20852-1776, U.S.A.; and that having an NCTC number is maintained in the Central Public Health Laboratory, Colindale Avenue, London, N.W. 9, England.

What is claimed is:

1. In a method for producing hyaluronic acid comprising contacting a hyaluronic acid-producing microorganism with a saccharide in a medium, the improvement which comprises:

adding to said medium at least one compound selected from the group consisting of phenol, cresol, xylenol, catechol, 4, methyl-pyrocatechol, urushiol, cresolcinol, orcinol, pyrogallol, 1, 2, 4-benzenetriol, benzenetetraol, benzenehexaol, getisinic acid, 2, 3-dihydroxybenzoic acid, gallic acid, salicylic acid, protocatechuic acid, pyrogallol-4-carboxylic acid, 3-o-galloylgallic acid, vanillin, o-vanillin, protocatechualdehyde, catechin, luteolin, myricetin, anthocyanidin, biphenyldiol, ellagic acid, naphthol, naphthalenediol, chrysarobin, anthragallol, sulfosalicylic acid, vitamin P, 3, 4-dihydroxyphenylalanine and tannins, in an amount of from 0.0001% by weight up to an amount such that the amount of hyaluronic acid produced in the presence of said compound is less than the amount of hyaluronic acid produced in the absence of said compound.

2. A method as set forth in claim 1, wherein a means to bring the microorganism into contact with saccharide is to grow the microorganism in the medium containing the saccharide as a nutrient source.

3. A method as set forth in claim 1, wherein a means to bring the microorganism into contact with saccharide is to bring the microorganism into contact with saccharide under non-culturing conditions.

* * * * *